(12) United States Patent
Thornes

(10) Patent No.: US 9,724,141 B2
(45) Date of Patent: Aug. 8, 2017

(54) BOLT APPARATUS

(75) Inventor: Brian Thornes, Dublin (IE)

(73) Assignee: Sota Orthopaedics Limited, Malahide, County Dublin (IE)

( * ) Notice: Subject to any disclaimer, the term of this patent is extended or adjusted under 35 U.S.C. 154(b) by 143 days.

(21) Appl. No.: 12/667,513

(22) PCT Filed: Jul. 3, 2008

(86) PCT No.: PCT/IE2008/000073
§ 371 (c)(1),
(2), (4) Date: Dec. 31, 2009

(87) PCT Pub. No.: WO2009/004603
PCT Pub. Date: Jan. 8, 2009

(65) Prior Publication Data
US 2010/0145396 A1    Jun. 10, 2010

(30) Foreign Application Priority Data

Jul. 3, 2007 (IE) .................................. S2007/0480
Feb. 15, 2008 (IE) .................................. S2008/0120

(51) Int. Cl.
*A61B 17/04* (2006.01)
*A61B 17/86* (2006.01)
(Continued)

(52) U.S. Cl.
CPC ........ *A61B 17/746* (2013.01); *A61B 17/7258* (2013.01)

(58) Field of Classification Search
CPC ............ A61B 17/7258; A61B 17/7266; A61B 17/746; A61B 17/844
(Continued)

(56) References Cited

U.S. PATENT DOCUMENTS 3,303,736 A * 2/1967 Raynovich, Jr. ................ 411/26
3,805,775 A * 4/1974 Fischer et al. .................. 606/68
(Continued)

FOREIGN PATENT DOCUMENTS

CA      990003     6/1976
WO      97/18769   5/1997
(Continued)

OTHER PUBLICATIONS

PCT/IE2008/000073, International Search Report.

*Primary Examiner* — Kevin T Truong
*Assistant Examiner* — Si Ming Ku
(74) *Attorney, Agent, or Firm* — Lathrop & Gage LLP

(57) ABSTRACT

The invention provides a bolt apparatus for fixation of bones, the bolt apparatus including an expandable section being having respective ends, the expandable section being operable between a contracted position and an expanded position; and expanding means in operable association with the expandable section, to displace the expandable section between the contracted position and the expanded position by simultaneously applying force to the respective ends of the expandable section, such that each of the respective ends of the expandable section are advanced toward the opposing respective end. The invention also provides a method for fixation of bones. The method includes the steps of reducing the fracture; providing a channel across the fracture; inserting a bolt apparatus of the invention; and fixing the bolt apparatus in the channel. Preferably, the method also includes providing a plate in operative association with the bolt.

21 Claims, 16 Drawing Sheets

(51) Int. Cl.
*A61F 2/08* (2006.01)
*A61B 17/74* (2006.01)
*A61B 17/72* (2006.01)

(58) Field of Classification Search
USPC .......... 606/62–68, 313, 309, 300, 301, 314, 606/326–329; 411/15–80.6; 623/17.11, 623/17.16
See application file for complete search history.

(56) References Cited

U.S. PATENT DOCUMENTS

| | | | |
|---|---|---|---|
| 4,236,512 A * | 12/1980 | Aginsky | 606/68 |
| 4,453,539 A * | 6/1984 | Raftopoulos | A61B 17/7258 606/63 |
| 5,059,193 A * | 10/1991 | Kuslich | F16B 13/061 606/247 |
| 5,759,184 A * | 6/1998 | Santangelo | 606/68 |
| 6,176,882 B1 * | 1/2001 | Biedermann et al. | 623/17.15 |
| 6,736,818 B2 * | 5/2004 | Perren et al. | 606/63 |
| 6,783,530 B1 * | 8/2004 | Levy | 606/63 |
| 2003/0078581 A1 * | 4/2003 | Frei et al. | 606/68 |
| 2003/0130660 A1 * | 7/2003 | Levy et al. | 606/63 |
| 2004/0133204 A1 * | 7/2004 | Davies | 606/63 |
| 2008/0147193 A1 * | 6/2008 | Matthis et al. | 623/17.16 |

FOREIGN PATENT DOCUMENTS

| | | |
|---|---|---|
| WO | 02/058575 | 8/2002 |
| WO | 03/007830 A1 | 1/2003 |
| WO | 2007/046691 | 4/2007 |

* cited by examiner

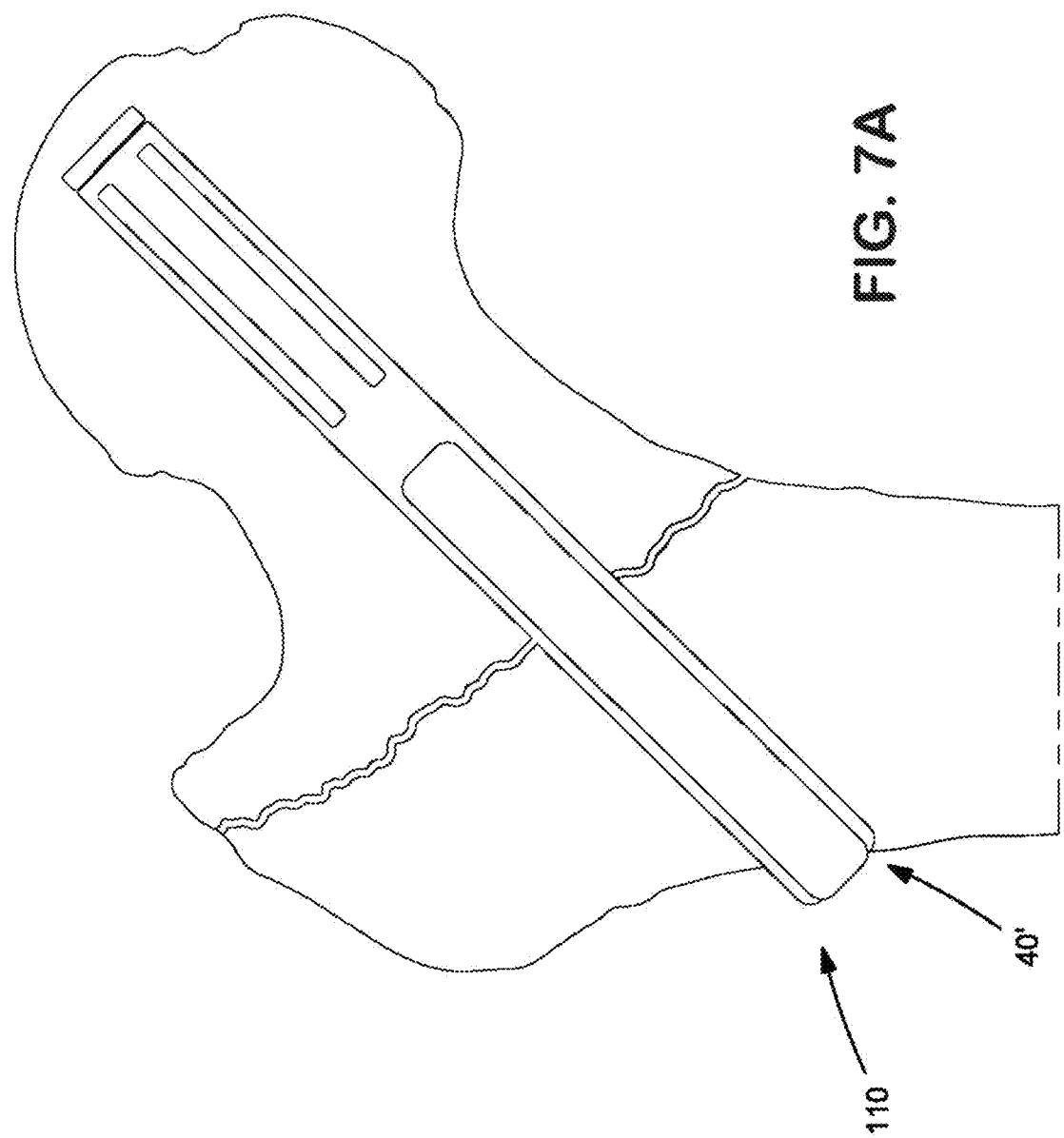

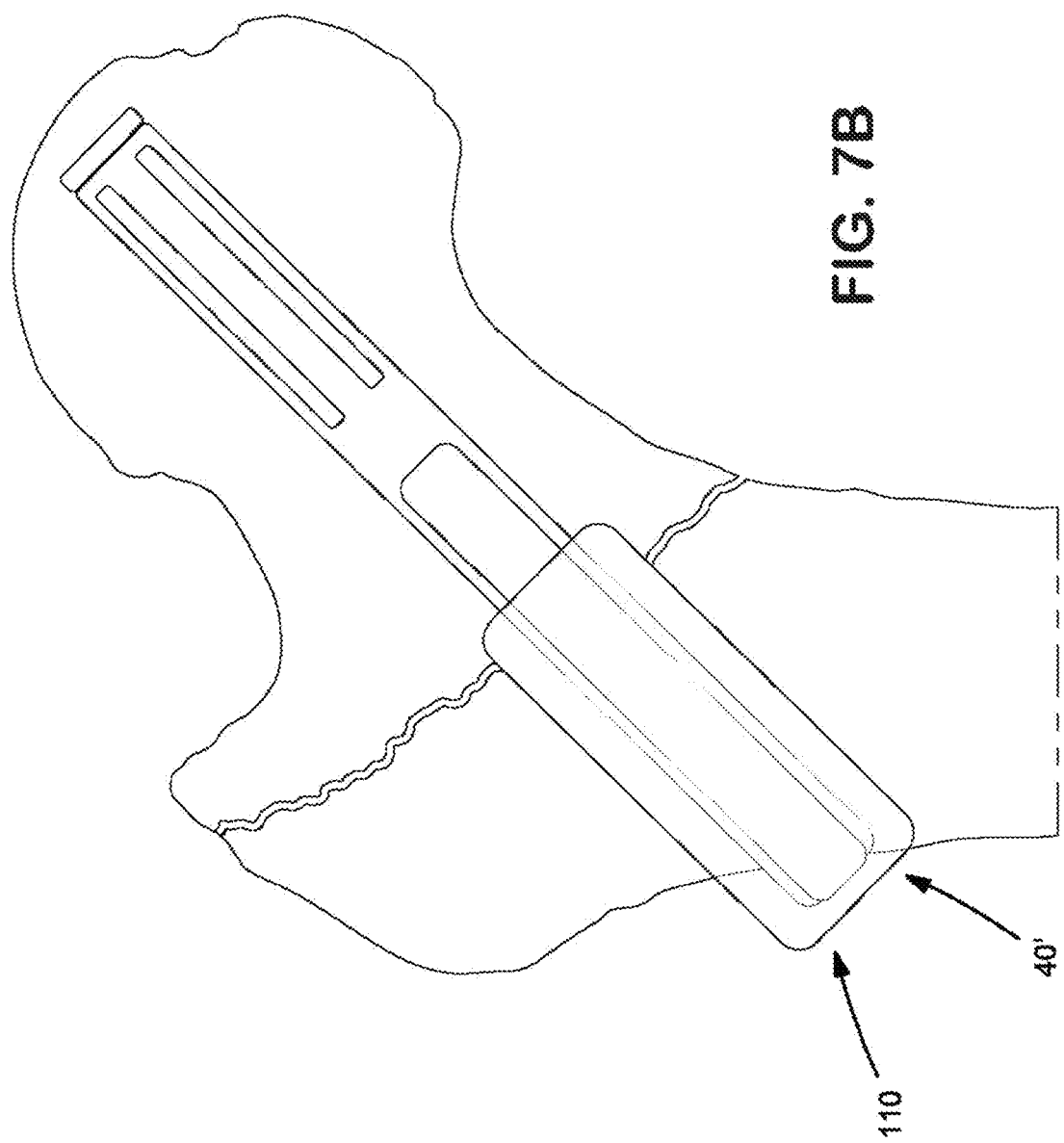

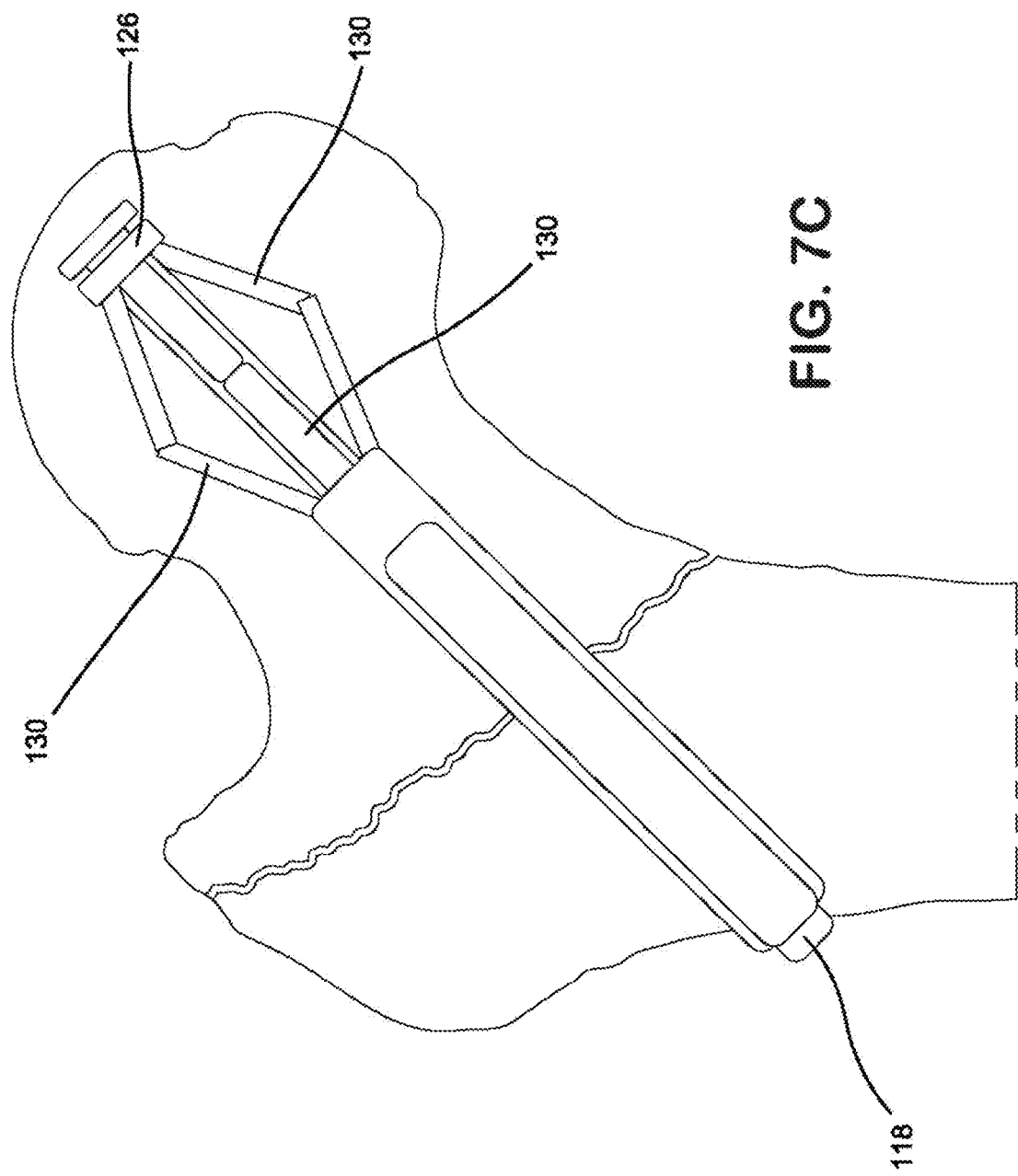

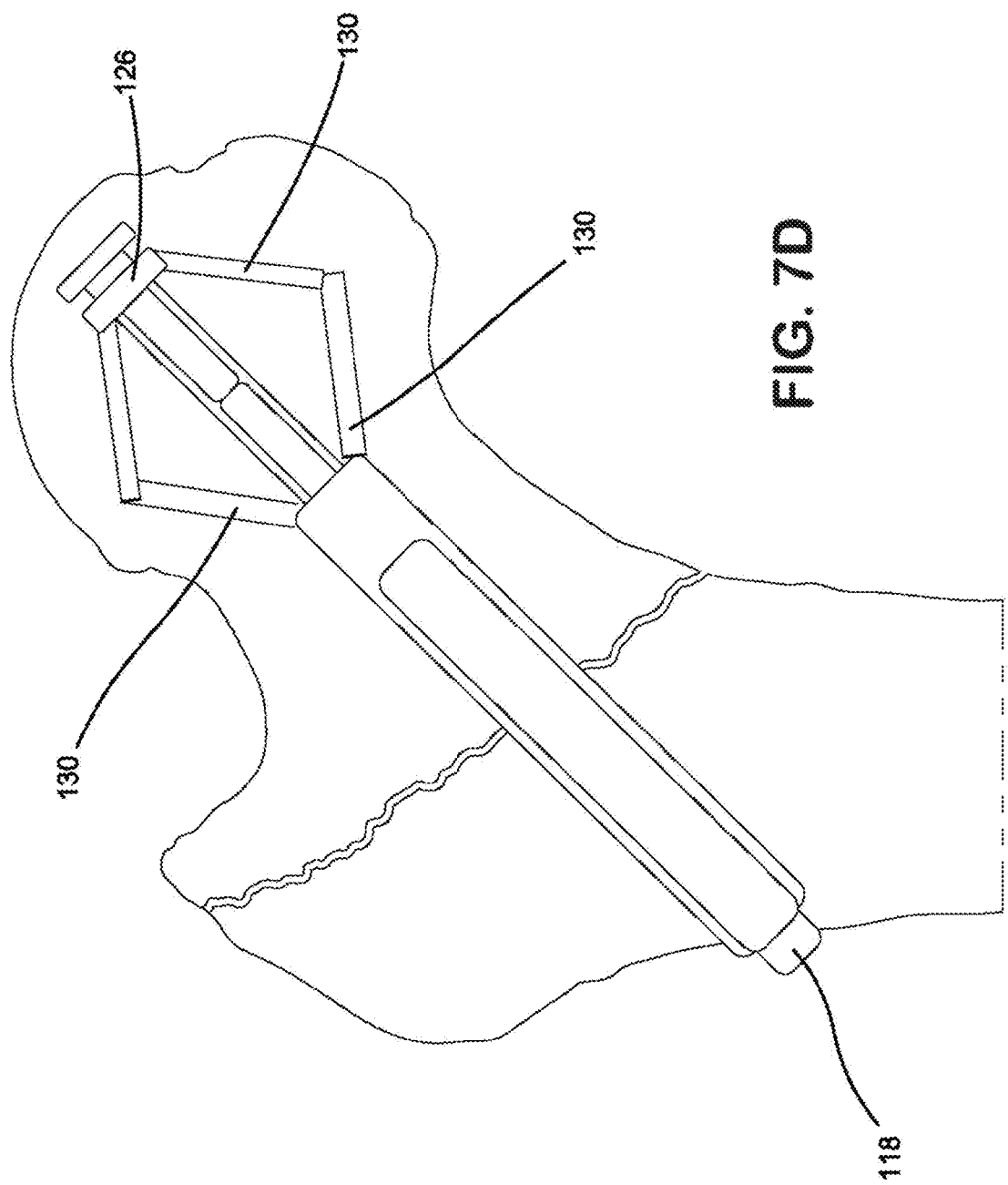

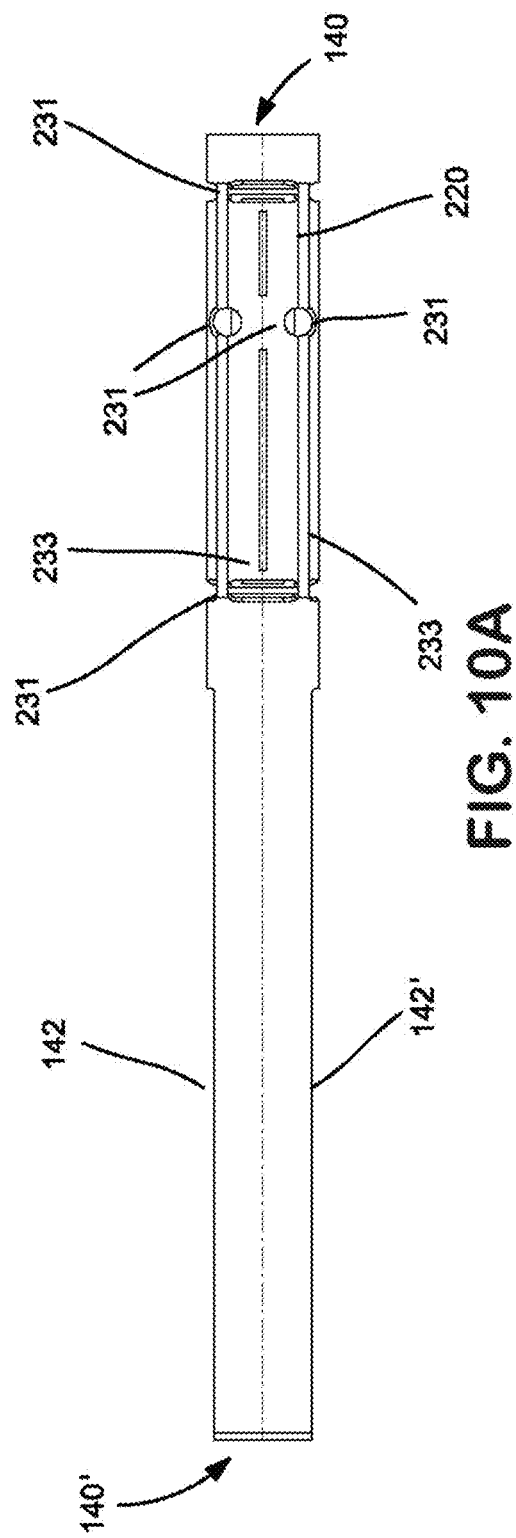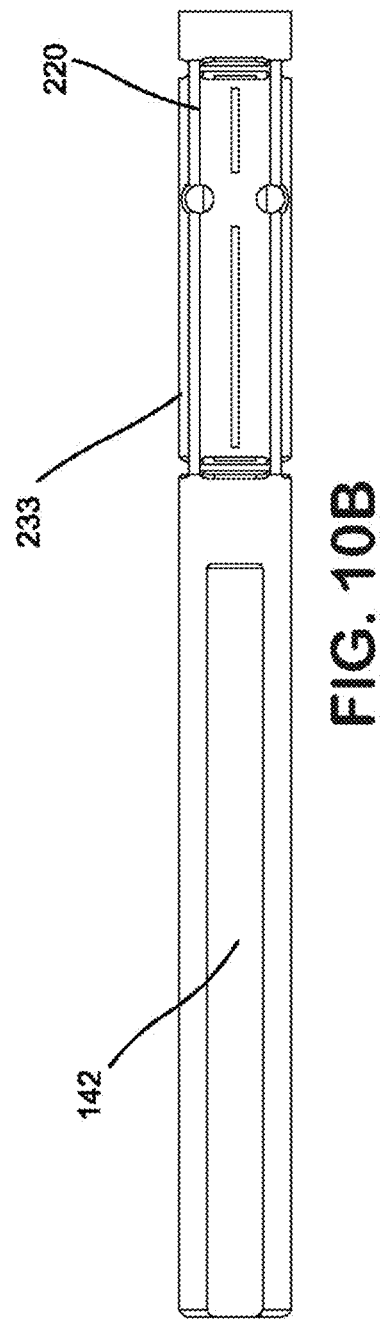
FIG. 10A
FIG. 10B

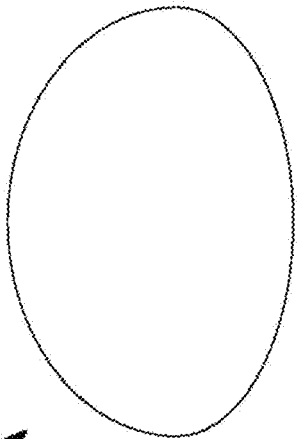
FIG. 12A
FIG. 12B
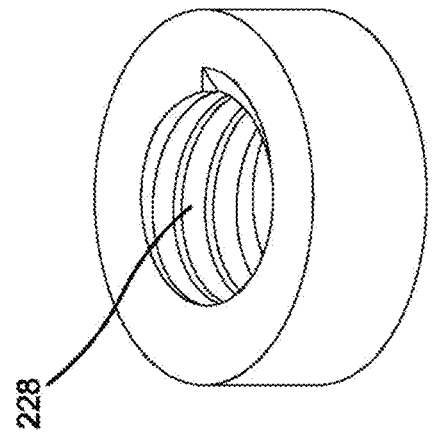
FIG. 11A
FIG. 11B

BOLT APPARATUS

CROSS-REFERENCE TO RELATED APPLICATIONS

This application is the U. S. National Stage of International Application No. PCT/IE2008/000073, filed Jul. 3, 2008, which claims the benefit of Irish Patent Application Nos. S2007/0480, filed Jul. 3, 2007, and S2008/0120, filed Feb. 15, 2008, all of which are hereby incorporated by reference to the extent not inconsistent with the disclosure herewith.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

The present invention relates to a bolt apparatus. In particular, the apparatus finds utility as a bolt apparatus for fixation of bones such as fractures of the femur, although it may be used in any suitable bone. By "bolt apparatus" is meant an apparatus that bolts or fixes objects together, which apparatus can be used for fixation of bones.

Bone fixation devices are well known and they find particular utility in the field of orthopaedic surgery, where they are used to fix a bone, which has sustained a fracture, across a fracture site. Generally, the type of fracture determines the type of surgery.

Patients with femoral neck fractures are treated with pinning or hip arthroplasty, depending on the age of the patient and the presence and degree of displacement. Patients with intertrochanteric fractures are treated with a sliding hip screw or an intramedullary hip screw, depending on the stability and location of the fracture.

If the fracture is stable, a sliding hip screw coupled to a side plate that is screwed onto the femoral shaft is used. The screw provides proximal fragment fixation. It is set inside a telescoping barrel that allows impaction of the bone, which promotes fracture union. A lateral buttress must be intact to stop excessive sliding of the screw.

When the direction of a fracture is parallel to the femoral neck, the fracture can be extremely unstable. This fracture type is called the reverse oblique pattern. A high rate of failure occurs if the fracture is treated with a sliding hip screw and a side plate. Because of the angle of the fracture, there is no bone laterally to stop the screw from sliding.

For unstable intertrochanteric fractures, including those of the reverse oblique pattern and those with subtrochanteric extension, an intramedullary hip screw is often indicated. This device combines a sliding hip screw with an intramedullary nail. Intramedullary hip screws can be placed through small incisions, and blood loss may be less than with a hip screw and side plate. The nail acts as a metal buttress to prevent sliding and provides better fixation in unstable fracture patterns.

Failure mechanisms of a hip screw include non-union, screw cut-out, nail breakage, malunion, and limp. Although sliding of the hip screw allows for bone compression and hopefully healing, it shortens the limb and causes abduction weakness. Most complications are subsequently treated with total hip arthroplasty.

BRIEF SUMMARY OF THE INVENTION

It is an object of the present invention to provide an improved device for bone fixation, which provides a means for reducing the occurrence of screw cut-out, amongst other failure mechanisms, thereby reducing the necessity of a patient having to undergo total hip arthroplasty.

According to a first aspect of the present invention there is provided a bolt apparatus for fixation of bones, the bolt apparatus comprising an expandable section having respective ends, the expandable section being operable between a contracted position and an expanded position; and expanding means in operable association with the expandable section, to displace the expandable section between the contracted position and the expanded position by applying force to the respective ends of the expandable section, such that each of the respective ends of the expandable section are advanced toward the opposing respective end.

Optionally, the expanding means displaces the expandable section between the contracted position and the expanded position by simultaneously applying force to the respective ends of the expandable section, such that each of the respective ends of the expandable section are advanced toward the opposing respective end.

As used herein, the term "advanced" is intended to mean the positive displacement of an object between a first position and a second position, wherein the first and second positions are different, spaced-apart positions. It is understood that, in the present invention, the first position of each respective end is the position when the expandable section is in the fully expanded position, and the second position of each respective end is the position when the expandable section is in the fully contracted position. Each respective end is displaced by the application of a force to each of the respective ends of the expandable section. Each respective end can optionally be simultaneously displaced by the simultaneous application of a force to each of the respective ends of the expandable section.

The present invention finds utility as a bolt apparatus for fixation of bones such as fractures of the femur, although it may be used in any suitable bone.

Optionally, the expanding means is in operable association with the expandable section, to displace the expandable section between the contracted position and the expanded position by applying force to the respective ends of the expandable section, such that each of the respective ends of the expandable section are independently advanced toward the opposing respective end. As used herein, the term "independently advanced" is intended to mean the positive and independent displacement of an object between a first position and a second position, wherein the first and second positions are different, spaced-apart positions. Each respective end is displaced by the application of a force to each of the respective ends of the expandable section. Each respective end can be displaced by the independent application of a force to each of the respective ends of the expandable section.

Further optionally, the expanding means is in operable association with the expandable section, to displace the expandable section between the contracted position and the expanded position by simultaneously applying force to the respective ends of the expandable section, such that each of the respective ends of the expandable section are independently advanced toward the opposing respective end. Each respective end is displaced by the application of a force to each of the respective ends of the expandable section. Each respective end can be optionally simultaneously displaced by the independent and simultaneous application of a force to each of the respective ends of the expandable section.

Preferably, the expanding means comprises a connecting means and at least two bodies mountable to the connecting means.

Preferably, the connecting means, for example, a shaft is adapted to allow reciprocal movement of the at least two bodies relative to the connecting means.

Preferably, the connecting means is a shaft.

Preferably, the at least two bodies are threadably mountable to the connecting means, for example, the shaft. Further preferably, first and second bodies are threadably mountable to the connecting means, for example, the shaft, and arranged for displacement in response to rotation of the connecting means, for example, the shaft to apply mechanical pressure to the respective ends of the expandable section. The connecting means, for example the shaft, can be arranged to simultaneously and independently apply mechanical pressure to the respective ends of the expandable section. The at least two bodies are displaced in response to rotation of the connecting means, for example, the shaft relative to one, both or each of the at least two bodies, or can be displaced by rotation of one, both or each of the at least two bodies relative to the connecting means, for example, the shaft.

Preferably, the connecting means, for example, the shaft comprises first and second threaded portions, wherein the threads of the first portion are of reverse orientation to the threads of the second portion.

Preferably, each of the first and second threaded portions has first and second terminal ends. Further preferably, the first terminal end corresponds to the first position, and the second terminal end corresponds to the second position, between which an object can be positively displaced. It is understood that, in this case, positive displacement means the reciprocal movement of the object between the first and second terminal ends of each threaded portion.

Preferably, the first body is mountable to the first threaded portion of the connecting means, for example, the shaft, and the second body is mountable to the second threaded portion of the connecting means, for example, the shaft.

Optionally, the first and second threaded portions are located adjacent one end, for example, a distal end of the connecting means, for example, the shaft. Alternatively, the first and second threaded portions are located adjacent respective opposing ends of the connecting means, for example, the shaft.

Preferably, the threaded portions of the connecting means, for example, the shaft are helically threaded portions.

Optionally, a proximal end of the connecting means, for example, the shaft is dimensioned and arranged, for example, by way of a transverse cross-section, so as to inhibit the coaxial rotation of the shaft relative to a set screw, once assembled.

Optionally, the proximal end of the connecting means, for example, the shaft is dimensioned and arranged, so as to provide means for delivering torque to the connecting means, for example, the shaft. Preferably, the proximal end of the connecting means, for example, the shaft is dimensioned and arranged to receive a torque delivery device such as a screwdriver, or similar device. Alternatively, the proximal end of the connecting means, for example, the shaft is dimensioned and arranged to allow rotation thereof by a hex key, or similar device. However, it will be appreciated that any shape of screwdriver to deliver the required torque may be used.

Optionally, at least one projection extends from the outer curved surface of the connecting means, for example, the shaft, to inhibit the coaxial rotation of the connecting means, for example, the shaft relative to a set screw, once assembled.

Preferably, each projection extends substantially radially from the curved surface of the connecting means, for example, the shaft.

Alternatively, the at least two bodies are arranged for displacement in response to rotation relative to the connecting means, for example, the shaft, by delivering torque to the at least two bodies. Optionally, at least the proximal end of the expanding means is dimensioned and arranged, so as to provide means for delivering torque to the at least two bodies.

Optionally, one, both, or each of the at least two bodies is engagable with at least one of the respective ends of the expandable section. Further optionally, one, both, or each of the at least two bodies is irreversibly engagable with at least one of the respective ends of the expandable section.

Optionally, one, both, or each of the at least two bodies is shaped and/or adapted to inhibit the coaxial rotation of the one, both, or each of the at least two bodies relative to the respective end of the expandable section.

Preferably, the expandable section is reversibly expandable. More preferably, the section is reversibly expandable under mechanical pressure.

Preferably, the expandable section is collapsible along its longitudinal axis. Further preferably, the expandable section is radially inwardly collapsible.

Preferably, the expandable section comprises at least two expandable members that extend from the longitudinal axis of the apparatus under mechanical pressure. More preferably, the expandable members extend radially from the longitudinal axis of the apparatus under mechanical pressure.

Preferably, each of the expandable members comprises a deformable arm.

Preferably, at least one point of folding is provided along each deformable arm.

Preferably, the or each point of folding comprises a point of weakness, a hinge mechanism, or any such mechanism that will facilitate the folding of the deformable arm at a desired location.

Optionally, the bolt apparatus further comprises a sleeve.

Preferably, the sleeve comprises a tube that is generally cylindrical in shape and is open at least at one end.

Preferably, the connecting means, for example, the shaft is locatable within the sleeve and rotatable coaxially therein.

Preferably, an outer surface of the sleeve has a transverse cross-section, so as to inhibit the coaxial rotation of the sleeve relative to the external bone with which it is in contact, once in use.

Alternatively, at least part of the surface of the sleeve is shaped or adapted, for example, by its transverse cross-section, so as to inhibit the coaxial rotation of the sleeve relative to the external bone with which it is in contact, once in use.

Optionally, the outer surface is generally hexagonal in transverse cross-section. This is thought to provide mechanical strength along the longitudinal axis of the outer sleeve. However, it will be seen that any shape that can impart the mechanical strength and restrict the rotation of the outer sleeve relative to the external bone with which it is in contact, may be used.

Alternatively or additionally, at least part of the surface of the sleeve is shaped and dimensioned to reversibly engage with a barrel of a plate. The plate can be a plate commonly used in the art, and will be selected by one skilled in the art. Preferably, at least part of the outer surface of the sleeve is planar in shape, for example, has a generally circular transverse cross-section but for a planar section, wherein the cross-section of the planar section is a rectilinear line.

Optionally, at least two apertures are provided in the sleeve.

Further optionally, the apertures are generally rectangular in shape and are substantially parallel to the longitudinal axis of the sleeve.

Preferably, the apertures run a pre-determined distance along the length of the sleeve. More preferably, the apertures run from adjacent an open distal end of the sleeve to approximately half the length of the sleeve. Alternatively, the apertures run from adjacent an open distal end of the up to approximately one third the length of the sleeve.

Alternatively, each of the expandable members is defined by the apertures running a pre-determined distance along the length of the sleeve.

Optionally, the expandable section and the sleeve are separate elements that are coterminous with each other.

Alternatively, the expandable section is integral to the outer sleeve.

Optionally, one, both, or each of the at least two bodies is engagable with at least part of the sleeve. Further optionally, one, both, or each of the at least two bodies is irreversibly engagable with at least part of the sleeve.

Optionally, one, both, or each of the at least two bodies is shaped and/or adapted to inhibit the coaxial rotation of the one, both, or each of the at least two bodies relative to the at least part of the sleeve.

Alternatively, at least one of the at least two (further optionally one or both) bodies defines a portion of the expandable section. Further optionally, at least one of the at least two (further optionally one or both) bodies comprises a screw thread located on a portion of the expandable section. Alternatively, at least one of the at least two (further optionally one or both) bodies defines a portion of the sleeve.

Optionally, at least one of the at least two (further optionally one or both) bodies comprises a screw thread located on at least part of the inner surface of the sleeve.

Preferably, a cap is provided to stop any component of the apparatus from advancing beyond the terminal end, preferably the distal terminal end, of the sleeve, when in use.

Preferably, the bolt apparatus is formed of a material that is suitable for sterilisation, so as to be provided in a sterile packaged state for use.

Preferably, the material is autoclavable.

Preferably the material is surgical stainless steel, but it will be seen that any material that is suitable for sterilisation and can impart the required mechanical strength may be used.

For the purposes of the present specification, a user is a person who will undertake the operation of the device during routine use. Usually, this will be a medical professional, where routine use includes fixation of a bone of a patient. When in use, the invention is oriented so as to have a proximal end and a distal end relative to said user.

A patient is defined as a person on whom the device will be used during routine operation.

According to a second aspect of the present invention, there is provided a method for fixation of bones, the method comprising the steps of reducing the fracture; providing a channel across the fracture; inserting a bolt apparatus according to the first aspect of the invention in the channel; and fixing the bolt apparatus in the channel.

Preferably, the fixing step comprises displacing the expandable section toward the expanded position by applying force to the respective ends of the expandable section, such that each of the respective ends of the expandable section are advanced toward the opposing respective end.

Preferably, the method comprises providing a plate in operative association with the bolt.

BRIEF DESCRIPTION OF THE SEVERAL VIEW OF THE DRAWINGS

Three embodiments of the invention will now be described, by way of example, with reference to the accompanying drawings, in which.

Figure 8:
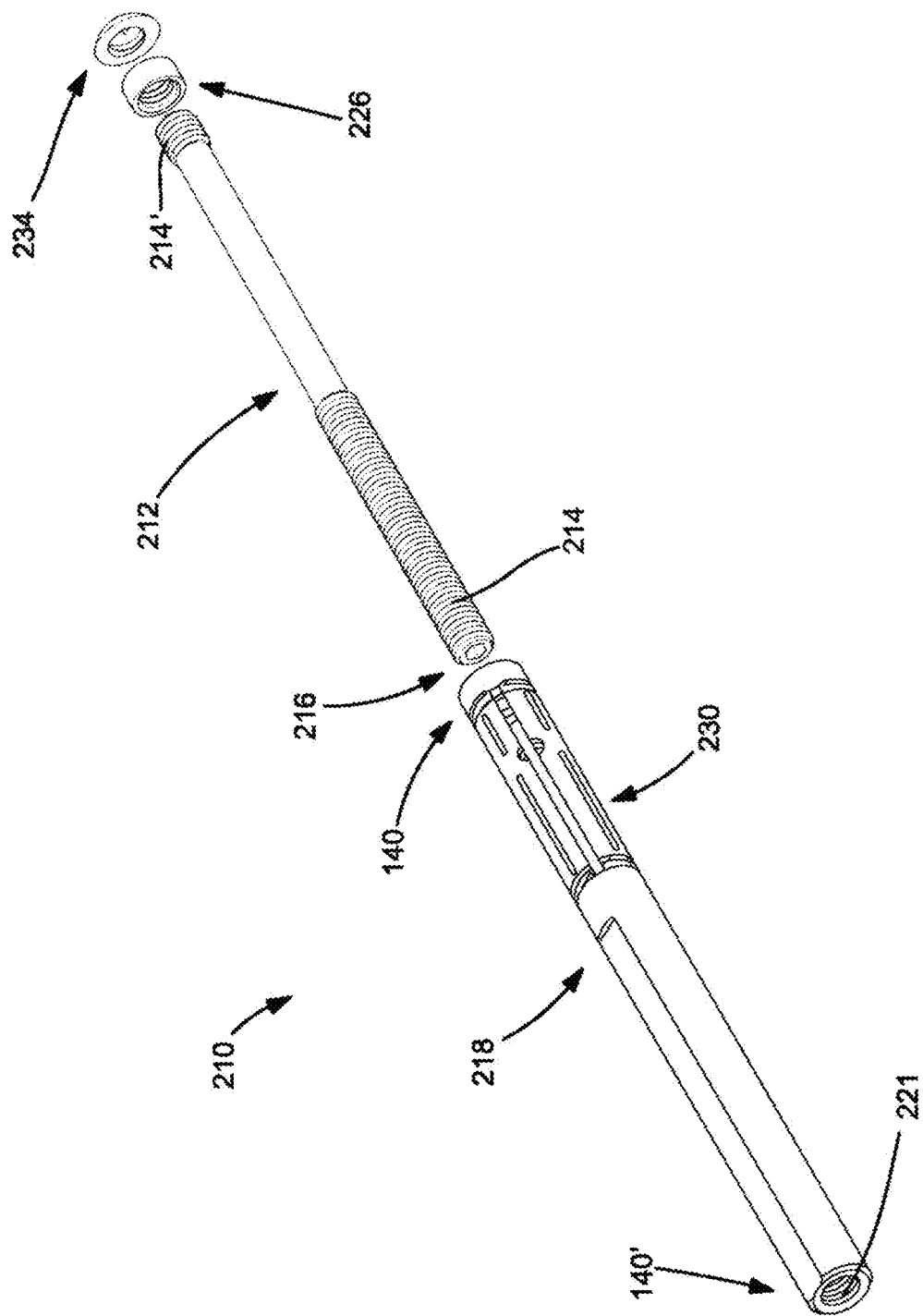
Figure 9:
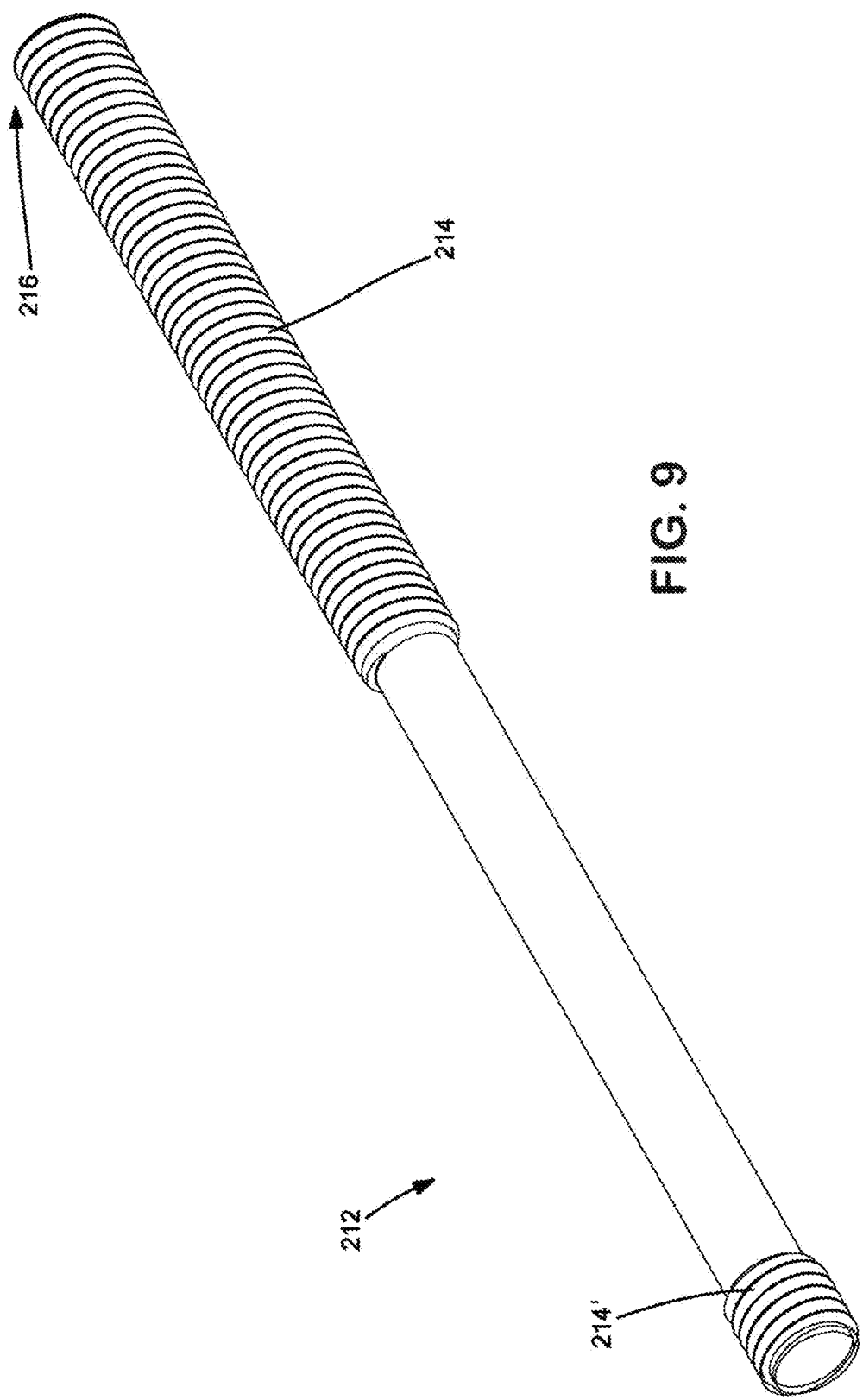

FIGS. 7A-F are schematic diagrams illustrating at least some of the steps involved in the use of a bolt apparatus according to a second embodiment of a second aspect of the present invention;

FIG. 8 is an exploded perspective view of a bolt apparatus according to a third embodiment of a first aspect of the present invention;

FIG. 9 is a perspective view of a connecting means of the bolt apparatus of FIG. 8;

FIG. 10A is a plan view of a sleeve of the bolt apparatus of FIG. 8;

FIG. 10B is a side view of the sleeve of FIG. 10A;

FIG. 11A is a vertical sectional view of a first mountable body of an expanding means of the bolt apparatus of FIG. 8;

FIG. 11B is a perspective view of the first mountable body of an expanding means of FIG. 11A;

FIG. 12A is a vertical sectional view of a cap of the bolt apparatus of FIG. 8; and FIG. 12B is a perspective view of the cap of FIG. 12A.

DETAILED DESCRIPTION OF THE INVENTION

In the drawings, similar reference numerals will be used to indicate like parts.

Figure 1:
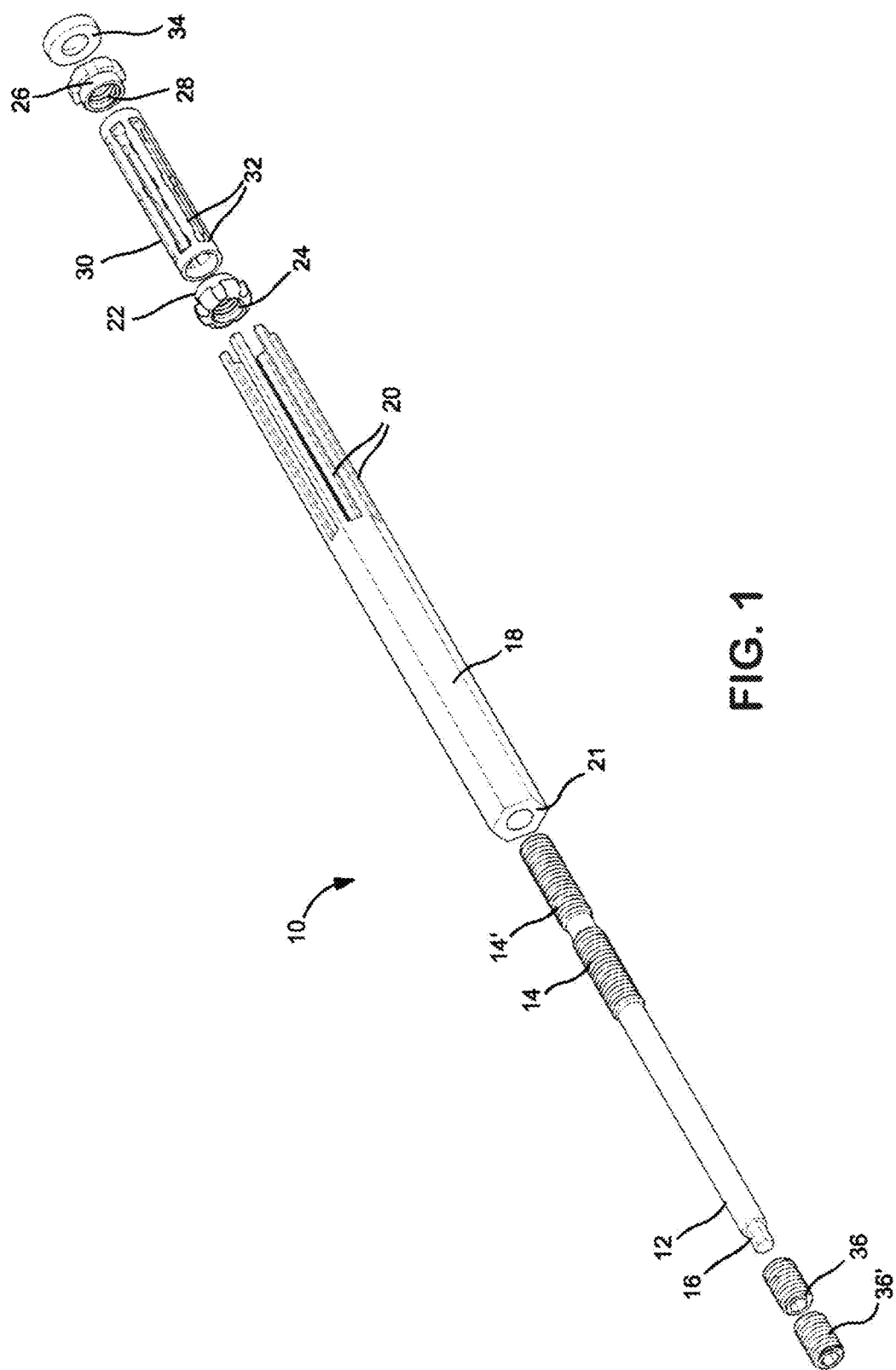
FIG. 1 is an exploded perspective view of a bolt apparatus according to a first embodiment of a first aspect of the present invention.

Referring now to FIG. 1 of the drawings, there is shown a bolt apparatus 10 according to a first embodiment of a first aspect of the invention. The bolt apparatus 10 comprises a connecting means, which is herein defined by a shaft 12; a sleeve 18; two mountable bodies, one proximal 22 and one distal 26; an expandable section 30; a cap 34; and two set screws, one proximal 36' and one distal 36.

The shaft 12 comprises an elongate member, which is generally cylindrical in shape. Two distinct helical screw threaded portions 14, 14' are provided adjacent the distal end of the shaft 12, wherein the relative orientation of each screw thread 14, 14' is opposite in direction to that of the other. The proximal end 16 of the shaft 12 is generally hexagonal in transverse cross-section.

The sleeve 18 comprises a tube, which is generally cylindrical in shape and is open at each end. The outer surface of the sleeve 18 is generally hexagonal in transverse cross-section, and the inner surface of the sleeve 18 is generally circular in transverse cross-section. The internal diameter of the sleeve 18 is generally of similar length to the external diameter of the shaft 12, whereby the shaft 12 can be located longitudinally and rotated coaxially within the sleeve 18.

A helical screw thread 21 is provided along a limited length of the inner surface of the sleeve 18. A generally rectangular aperture 20 is provided on each face of the outer surface of the sleeve 18, each of which apertures 20 extend along the longitudinal axis from the distal end to approximately half the length of the sleeve 18.

Two mountable bodies 22, 26 are provided, each of which is generally cylindrical in shape and is open at both ends. Each respective mountable body 22, 26 is of similar form, but has a helical screw thread that is oriented in the opposite direction relative to the other.

Figure 2:
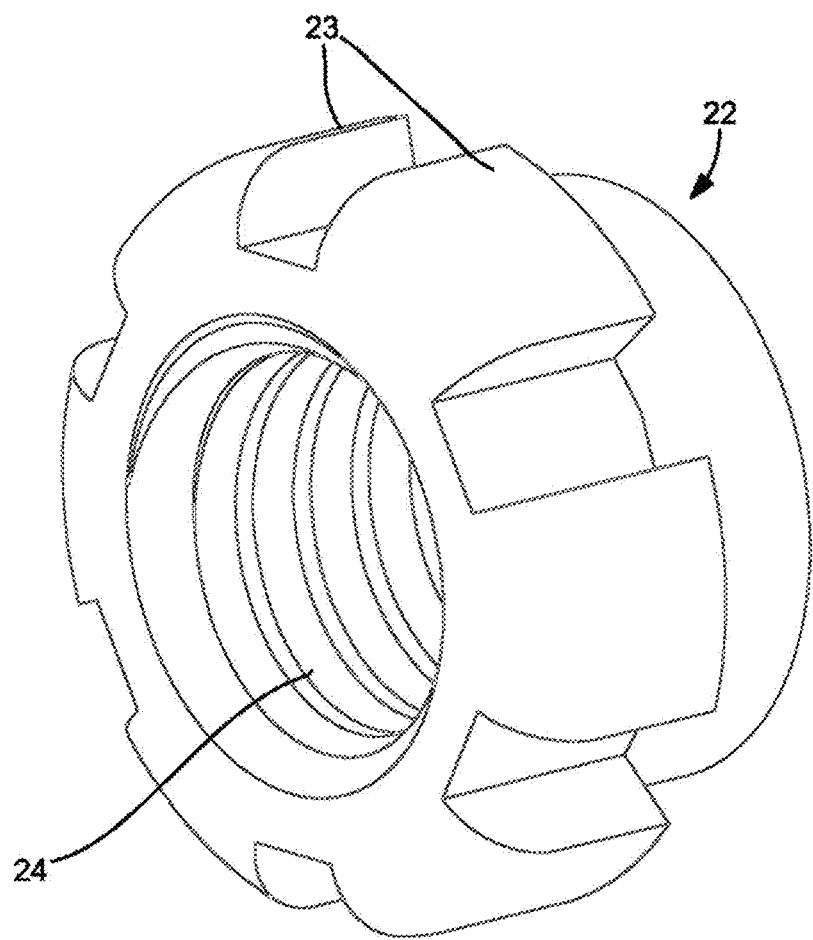
FIG. 2 is a perspective view of a first mountable body of an expanding means of the bolt apparatus of FIG. 1.

FIG. 2 is a perspective view of a first mountable body 22 of the bolt apparatus 10. A helical screw thread 24 is provided on the inner surface of the first mountable body 22. The internal diameter of the body 22 is generally of similar length to the external diameter of the shaft 12, whereby the screw thread 24 of the first mountable body 22 can engage with the screw threaded portion 14 of the shaft 12. A number of projections 23 are provided, each of which extend radially from the external surface of the mountable body 22. Each of the projections 23 is of a size and location so as to locate in each of the apertures 20 of the sleeve 18. A helical screw thread 28 is similarly provided (not shown in FIG. 2 but shown in FIG. 1) on the inner surface of the second mountable body 26. The internal diameter of the body 26 is generally of similar length to the external diameter of the shaft 12, whereby the screw thread 28 of the second mountable body 26 can engage with the screw threaded portion 14' of the shaft 12. A number of projections 23 are provided, each of which extend radially from the external surface of the mountable body 26. Each of the projections 23 is of a size and location so as to locate in each of the apertures 20 of the sleeve 18.

Figure 3A:
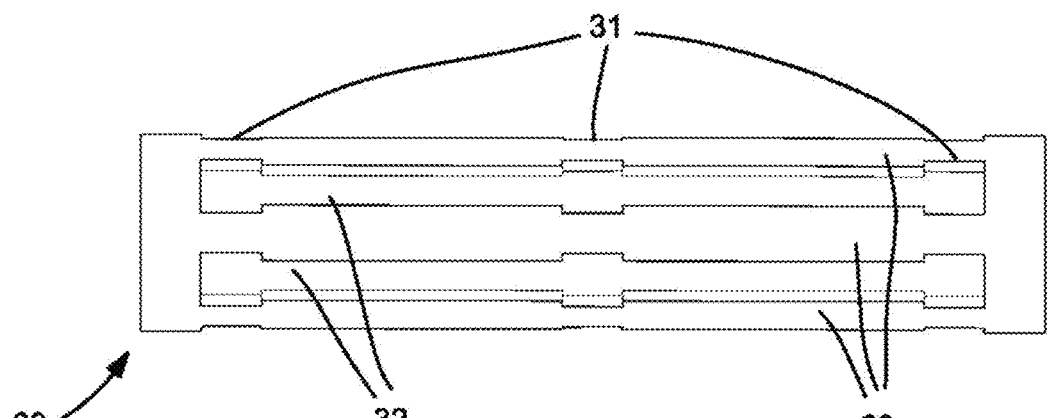
FIG. 3A is a side view of an expandable section of the bolt apparatus of FIG. 1.
Figure 3B:
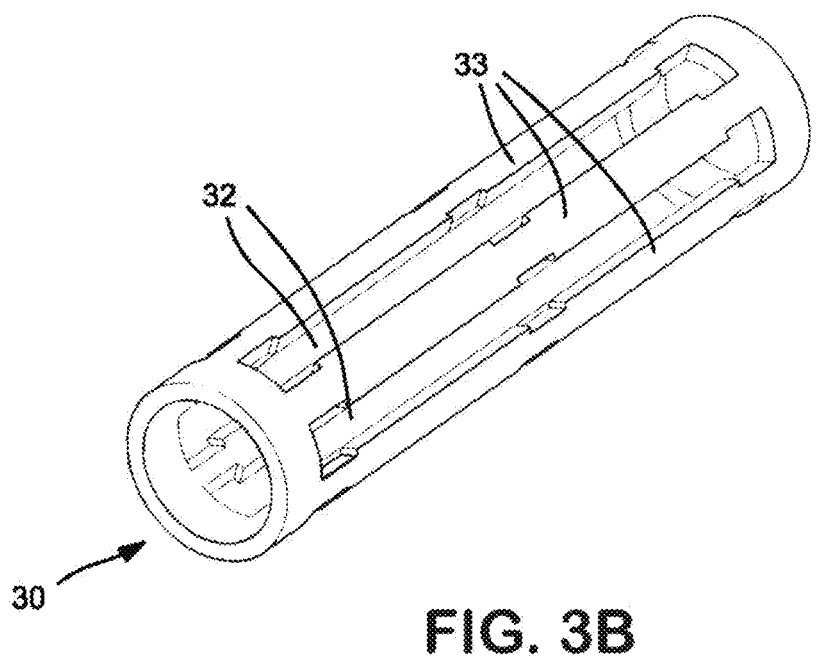
FIG. 3B is a perspective view of the expandable section of FIG. 3A.

FIGS. 3A and 3B are respectively side and perspective views of an expandable section 30 of the bolt apparatus 10, which comprises a generally cylindrically shaped tube, which is open at both ends. At least two generally rectangular apertures 32 are provided on the curved surface of the expandable section 30, each of which extends a limited length along the longitudinal axis of the expandable section 30. The area between the apertures defines deformable arms 33, the width of which is generally less than that of the apertures 20 of the sleeve 18, thereby allowing each of the deformable arms 33 of the expandable section 30 to extend radially through each of the apertures 20 of the sleeve 18, when in an in use, expanded state. A point of weakness 31 is provided at each of the respective ends of each deformable arm 33, where the deformable arm 33 is attached to the respective ends of the expandable section 30; and adjacent the centre point of the length of each deformable arm 33.

A cap 34, FIG. 1, is provided, wherein said cap is a disc, which is generally concave in transverse cross-section on one face. The cap 34 is provided for protection of the distal end of the bolt apparatus 10 during use, and is attached to the bolt apparatus 10 once assembled.

Figure 4:
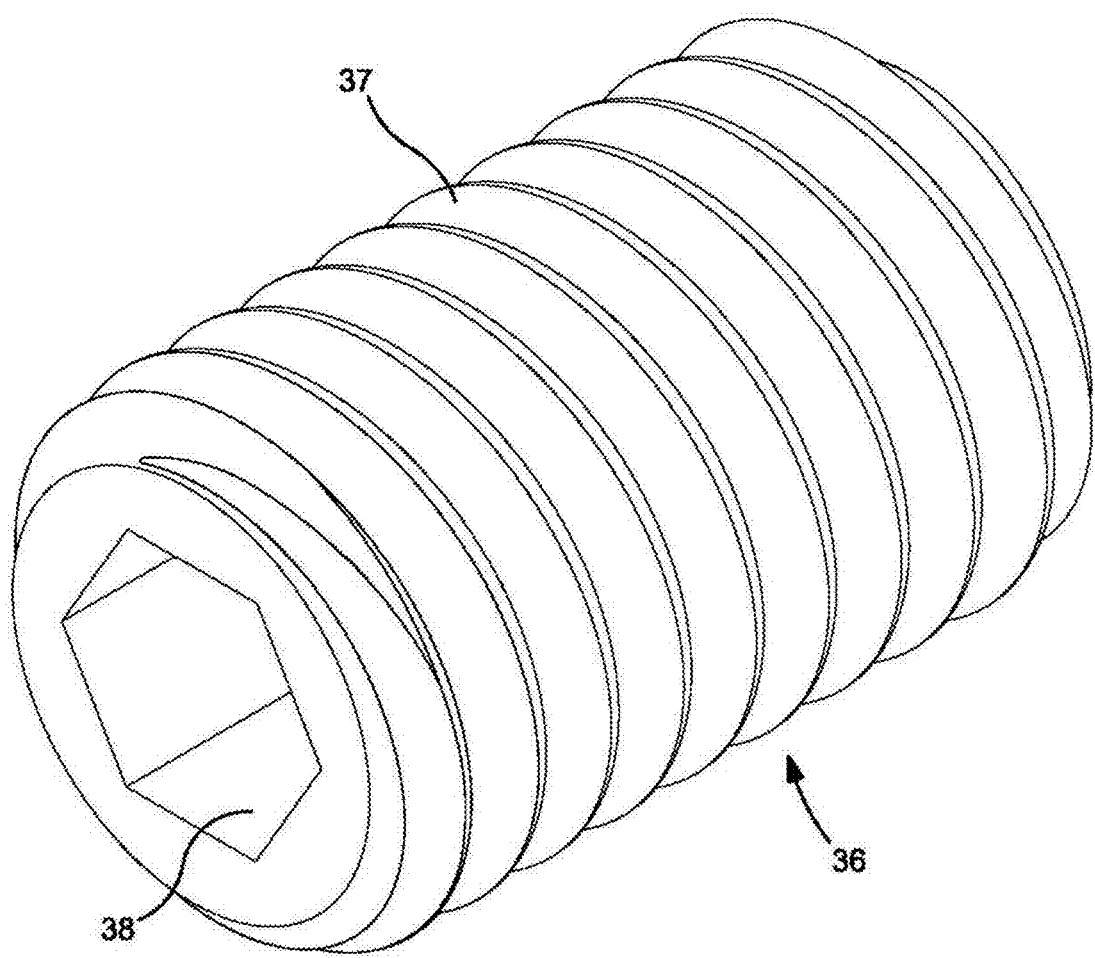
FIG. 4 is a perspective view of a set screw of the bolt apparatus of FIG. 1.

FIG. 4 is a perspective view of a set screw 36 (or 36') of the bolt apparatus 10, which comprises a generally cylindrically shaped member. A helical screw thread is provided on the outer surface 37 of the set screw 36. The external diameter of the set screw 36 is generally of similar length to the internal diameter of the unidirectional screw thread 21 of the inner surface of the sleeve 18, whereby the screw thread on the outer surface 37 of the set screw 36 can engage with the screw thread 21 of the inner surface of the sleeve 18.

An aperture 38, which is generally hexagonal in transverse cross-section, is provided along the longitudinal axis of the set screw 36, and extends the full length therethrough. The shape and diameter of the aperture 38 is so that the proximal end 16 of the shaft 12 can locate within the aperture 38 of the set screw 36.

Once assembled, each of the mountable bodies 22, 26 is located on one of the screw threaded portions 14, 14' of the shaft 12. Each of the mountable bodies 22, 26 is in tandem but opposite orientation relative to the other one, and is located at each respective end of the expandable section 30. Preferably, each of the mountable bodies 22, 26 is attached to each respective end of the expandable section 30 by an adherent means such as an adhesive.

The assembly comprising the shaft 12, mountable bodies 22, 26 and the expandable section 30 is located coaxially within the sleeve 18, wherein each of the projections 23 of each of the mountable bodies 22, 26 are substantially colinear with each of the deformable arms 33 of the expandable section 30 and the apertures 20 of the sleeve 18.

The cap 34 is attached to the distal end of the sleeve 18 by an adherent means such as an adhesive.

The distal set screw 36 engages with the proximal end 16 of the shaft 12, thereby providing a means by which to rotate the shaft 12, when in use.

Rotation of the shaft 12 within the sleeve 18 causes each of the mountable bodies 22, 26 to respectively advance along the screw threaded portions 14, 14', respectively, of the shaft 12. This applies mechanical pressure to the respective ends of the expandable section 30, wherein the respective ends are bought sequentially into closer proximity relative to one another, causing the deformable arms 33 of the expandable section 30 to deform at each of the points of weakness 31, and to expand radially from the longitudinal axis of the bolt assembly 10.

Once in an in use, expanded state the proximal set screw 36' is inserted into the proximal end of the sleeve 18 and can be rotated to provide a stop, which inhibits further rotation of the shaft 12 relative to the sleeve 18, therein assuring that the expandable section 30 does not collapse under external pressure from the surrounding bone, with which it is in contact.

Rotation of the shaft 12 in the opposite direction can ultimately cause the deformable arms 33 to retract toward the longitudinal axis of the bolt assembly 10, thereby facilitating the removal of the device, if required.

Figure 5:
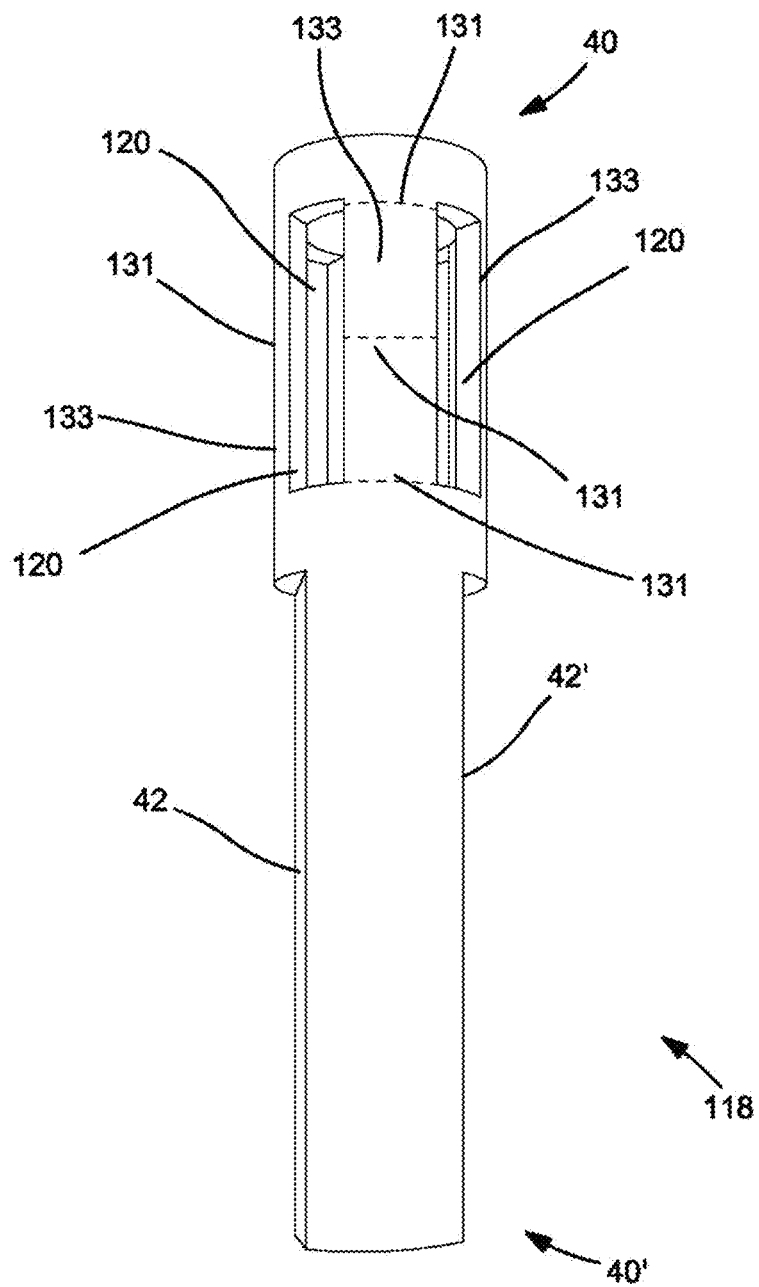
FIG. 5 is a perspective view of a sleeve of a bolt apparatus according to a second embodiment of a first aspect of the present invention.

FIG. 5 is a perspective view of a sleeve 118 of a bolt apparatus 110 according to a second embodiment of a first aspect of the present invention. The sleeve 118 comprises a tube, which is generally cylindrical in shape and having an, in use, distal end 40 and proximal end 40'. The outer surface of the sleeve 118 adjacent the distal end 40 is generally circular in transverse cross-section. The outer surface of the sleeve 118 adjacent the proximal end 40' is substantially curved having two opposing planar faces 42, 42'.

A number of generally rectangular apertures 120 are provided on the outer surface of the sleeve 118, each of which extend along the longitudinal axis from adjacent the distal end 40 to approximately one third the length of the sleeve 118. The area between the apertures 120 defines deformable arms 133, which form an expandable section 130, which is located coterminous to the sleeve 118. The deformable arms 133 extend radially from the longitudinal axis of the sleeve 118, when in an in use, expanded state. A point of weakness 131 is provided at each of the respective ends of each deformable arm 133, and at the centre point of the length of each deformable arm 133.

Figure 6:
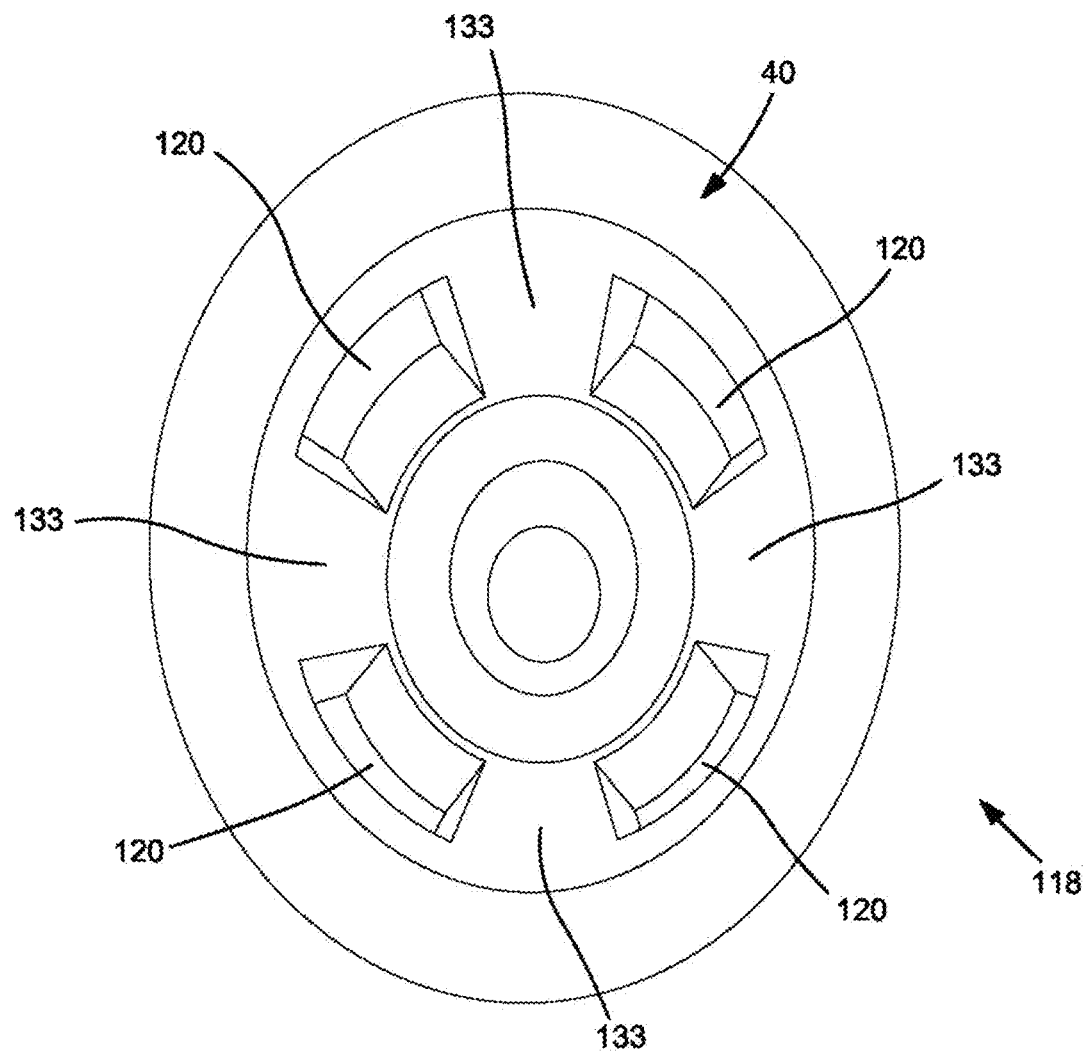
FIG. 6 is a distal end view at a slight angle from the longitudinal axis (thus, at a slight perspective) of the sleeve of FIG. 5.

FIG. 6 is a slightly perspective view from the distal end 40, at a slight angle from the longitudinal axis, of a sleeve 118 of a bolt apparatus 110 according to a second embodiment of a first aspect of the present invention. The inner surface of the sleeve 118 adjacent the proximal end 40' is generally circular in transverse cross-section. The internal diameter of the sleeve 118 adjacent the proximal end 40' is generally of similar length to the external diameter of the shaft 112 (not shown), whereby the shaft 112 can be located longitudinally and rotated coaxially within the sleeve 118. The inner surface of the sleeve 118 adjacent the distal end 40 is generally circular in transverse cross-section. The internal diameter of the sleeve 118 adjacent the distal end 40 is of a length to allow at least one of the mountable bodies 122, 126 (not shown) to locate coaxially within, and to irreversibly engage with, the lumen of the sleeve 118 adjacent the distal end 40.

Once assembled, each of the mountable bodies 122, 126 is located on each of the screw threaded portions 114, 114'(not shown) of the shaft 112. Each of the mountable bodies 122, 126 is in tandem but opposite orientation relative to the other one. The assembly comprising the shaft 112, and mountable bodies 122, 126 is located coaxially within the sleeve 118, wherein a first mountable body 122 is located adjacent the proximal end 40' of the sleeve 118, and is preferably attached thereto by an adherent means such as an adhesive; and a second mountable body 126 is located adjacent the distal end 40 of the sleeve 118, and is preferably attached thereto by an adherent means such as an adhesive and/or by compressive tension applied to the second mountable body 126 by the inner surface of the distal end 40 of the sleeve 118.

Rotation of the shaft 112 within the sleeve 118 causes each of the mountable bodies 122, 126 to advance along the screw threaded portions 114, 114' of the shaft 12, respectively. This applies mechanical pressure to the respective ends of the sleeve 118, wherein the respective ends are bought sequentially into closer proximity relative to one another, causing the deformable arms 133 of the expandable section 130 to deform at each of the points of weakness 131, and to expand radially from the longitudinal axis of the bolt assembly 110.

Once in an in use, expanded state the proximal set screw 136' (not shown) is inserted into the proximal end of the sleeve 118 and can be rotated to provide a stop, which inhibits further rotation of the shaft 112 relative to the sleeve 118, therein assuring that each of the deformable arms 133 does not collapse under external pressure from the surrounding bone, with which it is in contact.

Rotation of the shaft 112 in the opposite direction can ultimately cause the deformable arms 133 to retract toward the longitudinal axis of the bolt assembly 110, thereby facilitating the removal of the device, if required.

FIG. 8 is an exploded perspective view of a bolt apparatus 210 according to a third embodiment of a first aspect of the present invention. The bolt apparatus 210 comprises a shaft 212; a sleeve 218; a mountable body 226; an expandable section 230; and a cap 234.

The shaft 212, FIG. 9, comprises an elongate member, which is generally cylindrical in shape. Two distinct helical screw threaded portions 214, 214' are provided adjacent the respective ends of the shaft 212, wherein the relative orientation of each screw threaded portion 214, 214' is opposite in direction to that of the other. A hexagonal socket is provided at the proximal end 216 of the shaft 212, and is shaped and adapted to receive a hex key or similar torque delivery device.

The sleeve 218, FIGS. 10A and B, comprises a tube, which is generally cylindrical in shape and having an, in use, distal end 140 and proximal end 140'. The outer surface of the sleeve 218 adjacent the distal end 140 is generally circular in transverse cross-section. The outer surface of the sleeve 218 adjacent the proximal end 140' is substantially curved having two opposing planar faces 142, 142'.

An expandable section 230 is located adjacent the distal end 140 of the sleeve 218. The expandable section 230 comprises a number of generally rectangular apertures 220, which are provided on the outer surface of the sleeve 218, each of which extend along the longitudinal axis from adjacent the distal end 140 to approximately one third the length of the sleeve 218. The area between the apertures 220 defines deformable arms 233, which extend radially from the longitudinal axis of the sleeve 218, when in an in use, expanded state. A point of weakness 231 is provided at each of the respective ends of each deformable arm 233, and at the centre point of the length of each deformable arm 233.

Referring again to FIG. 8, the internal diameter of the sleeve 218 adjacent the proximal end 140' is generally of similar length to the external diameter of the shaft 212, whereby the shaft 212 can be located longitudinally and rotated coaxially within the sleeve 218. A helical screw thread 221 is provided along a limited length of the inner surface of the sleeve 218, extending at least part of the length from the proximal end 140' of the sleeve 218 to the expandable section 230. The helical screw thread 221 is engagable with the screw thread 214 of the shaft 212. The inner surface of the sleeve 218 adjacent the distal end 140 is generally circular in transverse cross-section. The internal diameter of the sleeve 218 adjacent the distal end 140 is of a length to allow the second mountable body 226 to locate coaxially within, and to irreversibly engage with, the lumen of the sleeve 218 adjacent the distal end 140. When engaged with the lumen at the distal end 140 of sleeve 218, the second mountable body 226 is inhibited from coaxially rotating relative to the sleeve 218, preferably by a press fit, but optionally by use of an adhesive.

A second mountable body 226, FIGS. 11A and B, is provided, which is generally cylindrical in shape and is open at both ends. A helical screw thread 228 is provided on the inner surface of the second mountable body 226. The internal diameter of the second mountable body 226 is generally of similar length to the external diameter of the shaft 212, whereby the screw thread 228 of the second mountable body 226 can engage with the screw threaded portion 214' of the shaft 212.

A cap 234, FIGS. 12A and B, is provided, wherein said cap is a disc, which is generally concave in transverse cross-section on one face. A screw-threaded socket 44 is located at the flat face of the cap 234. The internal diameter of the screw-threaded socket 44 is generally of similar length to the external diameter of the shaft 212, whereby the screw-threaded socket 44 can irreversibly engage with the terminal end of the screw threaded portion 214' of the shaft 212.

To assemble the bolt apparatus 210, the second mountable body 226 is located onto the screw threaded portion 214' of the shaft 212. The cap 234 is located onto the terminal end of the screw threaded portion 214'. The shaft 212 is then inserted coaxially into the lumen of the sleeve 218, and the screw threaded portion 214 of the shaft 212 is engaged with the helical screw thread 221 on the inner surface of the sleeve 218, such that the second mountable body 226 is located coaxially within, and irreversibly engages with, the lumen of the sleeve 218 adjacent the distal end 140.

In use, the shaft 212 is rotated using a hex key or similar torque delivery device, inserted into the hexagonal socket is provided at the proximal end 216 of the shaft 212. Rotation of the shaft 212 within the sleeve 218 causes the proximal end 140' of the sleeve 218 to advance along the screw threaded portion 214 of the shaft 212; and the second mountable body 226 to advance, in the opposite direction, along the screw threaded portion 214' of the shaft 212. This applies mechanical pressure to the respective ends of the expandable section 230, wherein the respective ends are bought sequentially into closer proximity relative to one another, causing the deformable arms 233 to deform at each of the points of weakness 231, and to expand radially from the longitudinal axis of the bolt assembly 210.

Rotation of the shaft 212 in the opposite direction can ultimately cause the deformable arms 233 to retract toward the longitudinal axis of the bolt assembly 210, thereby facilitating the removal of the device, if required.

Method of Surgery

The exposure and overall technique is similar to that used (as standard) for a dynamic hip screw. The conventional technique permits fixation of a wide variety of intertrochanteric, subtrochanteric and basilar neck fractures using, for example, a dynamic hip screw system provided by Synthes. Reference may be made to the Technique Guide produced by Synthes in this regard. However, an advantage to using the expanding hip bolt will be the possibility of utilising a minimally invasive technique, necessitating specialised instruments, to avoid the need for an open operation.

For the purposes of the present invention, a modified standard technique is described, as an alternative to the conventional technique. The patient is anaesthetised by general, regional or local anaesthesia, and placed supine on a standard fracture table. The leg is manipulated under x-ray fluoroscopy image intensifier to achieve a closed reduction. A longitudinal incision is placed (as in standard technique) on the lateral aspect of the thigh and the lateral part of the proximal femoral shaft is exposed using a combination of sharp and blunt dissection through the adipose tissue, fascia lata and vastus lateralis muscle.

Using a 2 mm guide wire with a 135 degree drill guide, the position for the proximal fixation is obtained. The optimum position for the expanding hip bolt is similar to that of a DHS lag screw, with the tip-apex distance being less than 5 mm on both AP and lateral views with the image intensifier. The hole for the bolt is drilled over the guide wire using a 9.25 mm drill bit. The wider drill-hole for the barrel at the lateral cortex is drilled using a 13 mm drill bit, over the guide wire. The proximal set screw 36' is removed from the assembled hip bolt apparatus and kept for later use.

An introducer with a distal threaded portion is screwed into the proximal threads 21 of the sleeve 18. The bolt assembly and introducer can be slid though the barrel of the plate to facilitate insertion of the plate onto the femur. The plate (with barrel) is inserted and positioned, so as the barrel fits into its proximal drill-hole and the distal plate sits on the lateral cortex of the femur. The plate is then fixed to the shaft of the femur via cortical screws through the distal holes of the plate.

The bolt assembly can be advanced though the barrel until in optimum position confirmed using the image intensifier. The deformable arms of the expandable section should not be deployed until the bolt assembly is in the optimum position, with the plate secured to the femur. The deformable arms are expanded using a torque hex-screwdriver, which rotates the shaft via the distal set screw, thus causing the mountable bodies 22, 26 to converge, compressing the expandable section. The torque hex-screwdriver has a torque limiter to prevent excessive torque force being applied to the bolt apparatus. The progress of the deformable arms expanding radially can be followed using the image intensifier. The screwdriver can be removed once the deformable arms have been deployed to an optimal position, as checked on the image intensifier or as limited by the torque limiter.

Fracture compression if necessary, can be performed by re-inserting the introducer into the bolt assembly and delivering controlled traction. Leg traction via the fracture table should be released prior to this manoeuvre. The proximal set screw, previously removed and kept, can be now re-inserted into the proximal end of the sleeve, using the hex-screwdriver. This tightens down onto the distal set screw, to prevent rotation or telescoping of the shaft. Final confirmation of the fixation is checked with the image intensifier, and the wound closed.

An alternative method of use of a second embodiment of the present invention will now be described, with reference to FIG. 7 of the drawings.

Using a 2 mm guide wire with a 135 degree drill guide, the position for the proximal fixation is obtained. The optimum position for the expanding hip bolt is similar to that of a DHS lag screw, with the tip-apex distance being less than 5 mm on both AP and lateral views with the image intensifier. The hole for the bolt assembly 110 is drilled over the guide wire using a 9.25 mm drill bit. The wider drill-hole for the barrel at the lateral cortex is drilled using a 13 mm drill bit, over the guide wire.

Figure 7E:
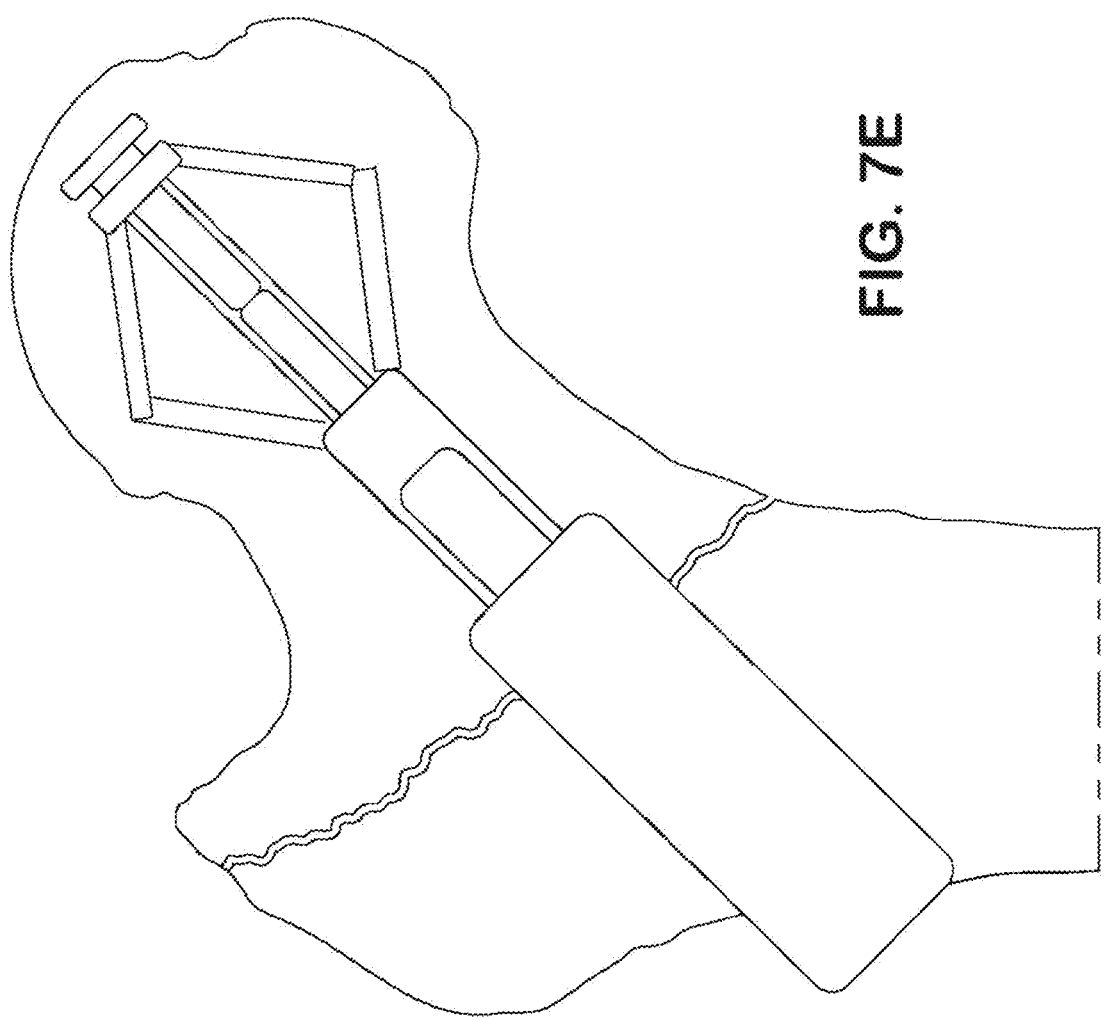
Figure 7F:
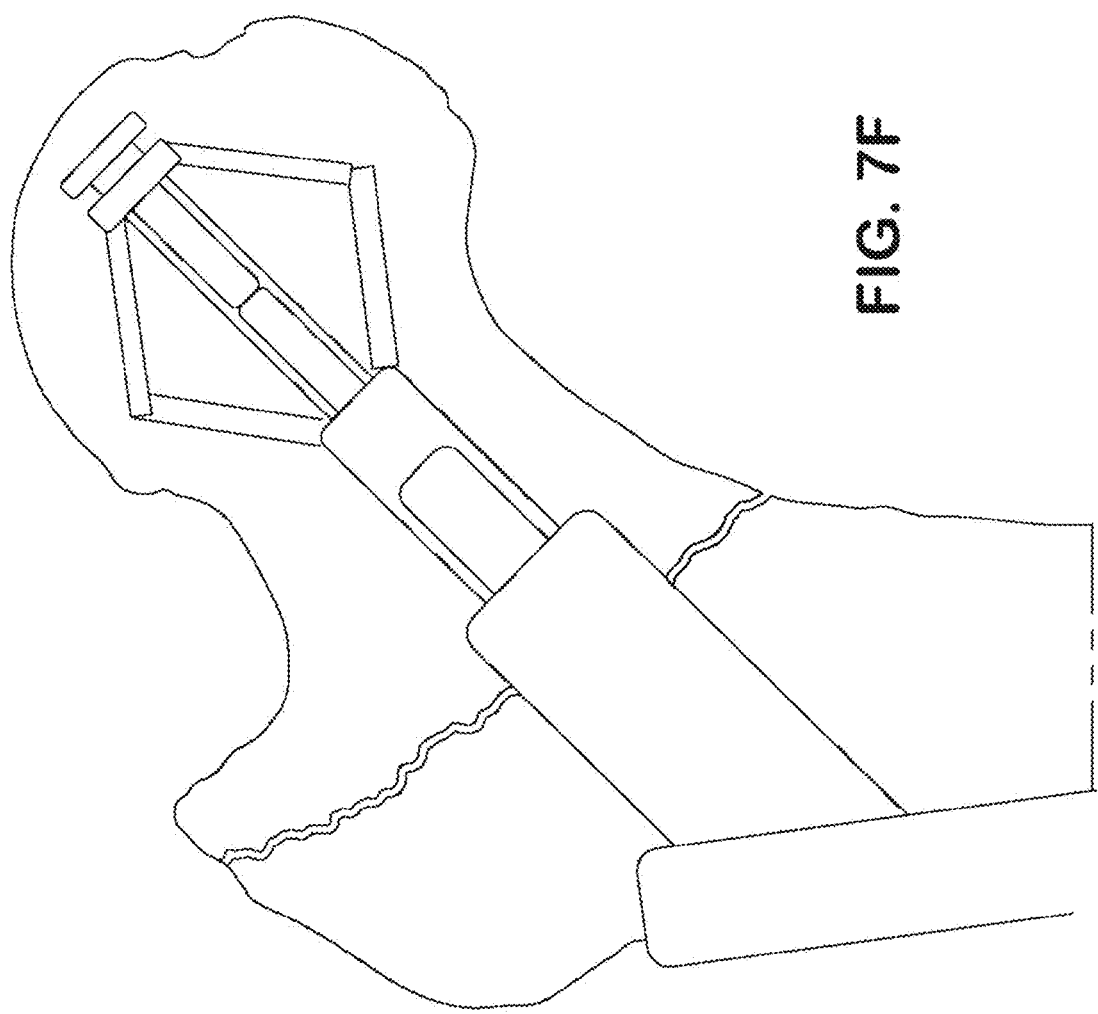

The bolt 110 can be advanced though the proximal drill hole until in optimum position confirmed using the image intensifier, FIG. 7A, ensuring that the proximal end 40' of the sleeve 118 is in the correct orientation to receive the barrel of a plate, FIG. 7B. The barrel of a plate can then be positioned and inserted on the proximal end 40' of the sleeve 118, FIG. 7B. The plate is then inserted and positioned, so as the barrel fits into its proximal drill-hole and the distal plate sits on the lateral cortex of the femur, FIGS. 7E & 7F. The plate is then fixed to the shaft of the femur via cortical screws through the distal holes of the plate.

The deformable arms 133 of the expandable section should not be deployed until the bolt assembly 110 is in the optimum position and rotation of the sleeve 118 is resisted by the barrel and plate that are securely fixed to the shaft of the femur. The deformable arms 133 are expanded using a torque screwdriver (not shown), which rotates the shaft 112, FIG. 7C, thus causing the mountable bodies 122, 126 to converge, compressing the expandable section 130, FIG. 7D. The torque screwdriver has a torque limiter to prevent excessive torque force being applied to the bolt assembly 110. The progress of the deformable arms 133 expanding radially can be followed using the image intensifier. The screwdriver can be removed once the arms have been deployed to an optimal position, as checked on the image intensifier or as limited by the torque limiter.

Final confirmation of the fixation is checked with the image intensifier, and the wound closed.

The above-mentioned alternative method of surgical use has now be described using the bolt apparatus of the second embodiment of the invention. It will, of course, be appreciated that the above-mentioned alternative method of surgical use can equally be employed with any other bolt apparatus of the invention, including those of the first and third embodiments of the first aspect of the invention.

The invention is not limited to the embodiments described herein but can be amended or modified without departing from the scope of the present invention.

The invention claimed is:

1. A bolt apparatus for fixation of bones, the bolt apparatus comprising an expandable section having respective ends, the expandable section being operable between a contracted position and an expanded position; and expanding means comprising a connecting means and at least two bodies mountable to the connecting means; wherein the connecting means is a shaft rotatable about a single longitudinal axis of the bolt apparatus and comprising first and second threaded portions and wherein threads of the first portion are of reverse orientation to threads of the second portion; wherein the expanding means is in operable association with the expandable section to displace the expandable section between the contracted position and the expanded position by applying force to the respective ends of the expandable section, such that each of the respective ends of the expandable section is simultaneously displaced toward the opposing respective end, wherein the expandable section is reversibly expandable, wherein the expandable section comprises at least two deformable arms that extend radially from a longitudinal axis of the bolt apparatus under mechanical pressure, wherein at least one point of folding is provided along each deformable arm, and wherein one, both, or each of the at least two bodies is attached to the expandable section by compressive tension applied to the one, both, or each of the at least two bodies by an inner surface of the expandable section.

2. A bolt apparatus according to claim 1, wherein the at least two bodies are threadably mountable to the connecting means, and arranged for displacement in response to rotation of the connecting means to apply mechanical pressure to the respective ends of the expandable section.

3. A bolt apparatus according to claim 1, wherein a first body of the at least two bodies is mountable to the first threaded portion of the connecting means, and a second body of the at least two bodies is mountable to the second threaded portion of the connecting means.

4. A bolt apparatus according to claim 1, wherein at least one of the at least two bodies defines a portion of the expandable section.

5. A bolt apparatus according to claim 4, wherein at least one of the at least two bodies comprises a screw thread located on at least part of the inner surface of the expandable section.

6. A bolt apparatus according to claim 1 further comprising a sleeve.

7. A bolt apparatus according to claim 6, wherein the expandable section and the sleeve are separate elements.

8. A bolt apparatus according to claim 6, wherein the expandable section is integral to the sleeve.

9. A bolt apparatus according to claim 6, wherein at least part of a surface of the sleeve is shaped or adapted to inhibit coaxial rotation of the sleeve or the expandable section relative to the bone with which it is in contact, once in use.

10. A bolt apparatus according to claim 6, wherein at least part of an outer surface of the sleeve or the expandable section is shaped and dimensioned to reversibly engage with at least part of a further bone fixation device, for example, a barrel of a plate.

11. A bolt apparatus according to claim 6, wherein at least one of the at least two bodies is engagable with at least part of the sleeve.

12. A bolt apparatus according to claim 6, wherein at least one of the at least two bodies defines a portion of the sleeve.

13. A bolt apparatus according to claim 6, wherein at least one of the at least two bodies comprises a screw thread located on at least part of the inner surface of the sleeve.

14. A method for fixation of bones, the method comprising the steps of reducing a fracture; providing a channel across the fracture; inserting a bolt apparatus according to claim 1 in the channel; and fixing the bolt apparatus in the channel.

15. A method according to claim 14, wherein the fixing step comprises displacing the expandable section toward the expanded position by applying force to the respective ends of the expandable section, such that each of the respective ends of the expandable section are advanced toward the opposing respective end.

16. A method according to claim 15, wherein the method further comprises the step of providing a further bone fixation device, such as a plate, in operative association with the bolt apparatus.

17. A bolt apparatus according to claim 1, wherein the expandable section comprises four deformable arms.

18. A bolt apparatus according to claim 1, wherein the or each point of folding comprises a point of weakness, a hinge mechanism, or any such mechanism that will facilitate the folding of the deformable arm at a desired location.

19. A bolt apparatus according to claim 1, wherein the or each point of folding comprises a point of weakness, and a point of weakness is provided at each of the respective ends of each deformable arm, and at a centre point of a length of each deformable arm.

20. A bolt apparatus according to claim 1, wherein a first body of the at least two bodies is attached to the expandable section by the compressive tension applied to the first body by the inner surface of the expandable section; and wherein a second body of the at least two bodies comprises a screw thread located on at least part of the inner surface of the expandable section.

21. A bolt apparatus according to claim 1, wherein at least part of a surface of the expandable section is shaped or adapted to inhibit coaxial rotation of the expandable section relative to an external bone with which it is in contact during use.

* * * * *